United States Patent [19]

De Munck et al.

[11] 4,434,302
[45] Feb. 28, 1984

[54] PROCESS AND CATALYST FOR PERFORMING HYDROFORMYLATION REACTIONS

[75] Inventors: Nicolaas A. De Munck, Delft; Joseph J. F. Scholten, Sittard, both of Netherlands

[73] Assignee: Stamicarbon B.V., Geleen, Netherlands

[21] Appl. No.: 265,222

[22] Filed: May 19, 1981

[30] Foreign Application Priority Data

May 28, 1980 [NL] Netherlands .......................... 8003059

[51] Int. Cl.$^3$ ........................ B01J 31/08; B01J 31/10; C07C 5/24
[52] U.S. Cl. .................................. 568/454; 260/429 J; 585/665; 525/340; 502/155; 502/159
[58] Field of Search ................. 252/431 P; 260/429 J; 585/665; 525/340; 568/454

[56] References Cited

U.S. PATENT DOCUMENTS

| | | | |
|---|---|---|---|
| 3,671,597 | 6/1972 | Kroll | 585/665 |
| 3,855,307 | 12/1974 | Rony et al. | 585/665 |
| 3,998,864 | 12/1976 | Trevillyah | 252/431 P |
| 4,007,318 | 2/1977 | Mango et al. | 525/340 |
| 4,009,003 | 2/1977 | Stautzenberger et al. | 252/431 P |
| 4,098,727 | 7/1978 | Haag et al. | 525/340 |
| 4,111,856 | 9/1978 | Haag et al. | 525/340 |
| 4,179,403 | 12/1979 | Kim et al. | 508/454 |
| 4,297,239 | 10/1981 | Bryant et al. | 252/431 P |

*Primary Examiner*—Natalie Trousof
*Assistant Examiner*—Raymond Covington
*Attorney, Agent, or Firm*—Cushman, Darby & Cushman

[57] ABSTRACT

A catalyst and process for making same which is used for hydroformylation reactions by the conversion of an olifically unsaturated compound. The catalyst is prepared by the phosphochlorination of the polymer carrier in the presence of borontrifluoride or a borontrifluoride complex. The chlorophosphonyl groups are converted into phosphine or phosphite groups and the resultant groups are reacted with a catalytically active metal complex.

8 Claims, No Drawings

PROCESS AND CATALYST FOR PERFORMING HYDROFORMYLATION REACTIONS

BACKGROUND OF THE INVENTION

The invention relates to a process and a catalyst for performing hydroformylation reactions by conversion of an olefinically unsaturated compound with hydrogen and carbon monoxide in the presence of a catalytically active organometallic complex, in particular a rhodium or platinum complex.

It is known to perform such a hydroformylation as a homogeneously catalytic reaction, with the organometallic complex dissolved in an inert solvent or in a solvent that can act as a ligand and for the metal. The disadvantage attaching to this process is that problems may arise in connection with loss of catalyst and in the subsequent processing of the reaction products.

It has also been proposed to perform the hydromylation as a heterogeneously catalytic reaction, using a catalyst consisting of a porous solid carrier material which has within its pores a solution of the catalytically active metal complex in a solvent. These catalysts are stable and may have great selectivity, but the activity per unit weight of metal is relatively low. It has even been proposed to immobilize the catalytically active complex by binding it to a solid carrier through the intermediacy of a group acting as ligand. This type of catalyst has until now been used for hydroformylation in the liquid phase.

OBJECT OF THE INVENTION

The object of the invention is to overcome these known disadvantages by means of hydroformylation wherein the catalyst is stable and has a high activity per unit weight of metal.

SUMMARY OF THE INVENTION

According to the present invention an olefinically unsaturated compound can be converted with carbon monoxide and hydrogen at an elevated temperature in the presence of a catalyst comprising a macroreticular organic polymer containing phosphine or phosphite groups which act as ligands for a catalytically active organometallic complex. This conversion is conducted in the gas phase in the presence of a catalyst. The carrier of the catalyst comprises a polymer into which phosphine or phosphite groups have been introduced by phosphochlorination of the polymer in the presence of borontrifluoride or a borontrifluoride complex. Thereafter, the chlorophosphonyl groups are converted into phosphine or phosphite groups and the groups so formed are then reacted with the catalytically active metal complex.

These catalysts are very stable and possess a high activity per unit weight of metal. The resulting reaction products are easy to recover with little or no loss of catalyst.

DETAILED DESCRIPTION OF THE INVENTION

The carrier for the catalyst may be any macroporous polymer amenable to phosphochlorination, with polystyrene cross-linked with divinylbenzene being preferable. Preferably, the carrier material is thoroughly washed before the phosphochlorination and dried in order to remove catalyst and monomer residues from the resin. The polymer can be used in the form of particles having a size of, e.g., between about 0.1 and about 5 mm.

The properties of the catalyst depend on the way in which the phosphine or phosphite groups have been applied to the carrier material. According to the present invention, the carrier material is reacted preferably with phosphorus trichloride in the presence of borontrifluoride or a borontrifluoride complex, e.g. borontrifluoride etherate, as the catalyst. After this phosphochlorination the material is washed to remove unconverted phosphorus trichloride and boron catalyst. Next, the $PCl_2$ groups bound to the polymer are converted into phosphine or phosphite groups by reacting the phosphochlorinated resin with an (earth)alkali hydrocarbon compound or an (earth)alkali alcoholate.

Suitable alkali hydrocarbon compounds are alkalialkyl compounds such as ethyllithium, n-butyllithium, ethylsodium, cyclohexyllithium, and alkaliaryl compounds such as phenyllithium, phenylpotassium, benzyllithium, toluyllithium and alpha- or beta-naphthyllithium.

The alcoholates may be derived from aliphatic monoalcohols or from monofunctional phenolic compounds. Examples of suitable alcoholates are lithiummethanolate, sodiumbutanolate, lithiumhexanolate and lithiumphenolate. For the introduction of phosphite groups alkali alcoholates derived from unbranched aliphatic monoalcohols are preferable. Arylalkali compounds are preferably used for producing phosphine groups.

At elevated temperature, e.g. between about 50° and about 90° C., the conversion proceeds to completion. The resulting resin, containing phosphine or phosphite groups, is washed and dried. Thereafter this resin is reacted with a solution of a compound or complex of a transition metal. Preferably this reaction is carried out with hydrogen as a protective gas. If carbon monoxide or nitrogen is used as the protective gas, the resultant catalyst are less stable. By preference, the resin is reacted with a solution of a complex of the metal. Very suitable for this purpose are the organometallic complexes containing at least one ligand that is readily replaceable by a phosphine or phosphite group.

The central metal atom in the organometallic complex is selected from the transition metals of the groups V, VI, and VII and VIII of the periodic system according to Mendeleev, such as Re, Fe, Ru, Os, Co, Rh, Ir, Ni, Pd and Pt, and in particular rhodium, platinum, cobalt, ruthenium and iridium. Mixtures of these metals may also be used.

Eligible as ligands in the above-mentioned organometallic complex are, besides such ligands as CO, H and $\sigma$- and $\pi$-bonded alkenes, organic compounds comprising in their molecule an atom from the groups VB and VIB of the periodic system according to Mendeleev which contains a free electron pair, e.g. P, S, B, Se, Te, Sb, As. Also suitable are, for example, the halogenides, such as Cl, Br and I, tin halides and germanium II halides, acid radicals such as acetate, propionate, and easily transposable ligands such as acetylacetonate, hydrogen, carbon monoxide, tetrahydrofuran and diolefine. Examples of suitable organometallics are rhodiumhydridocarbonyltris(triphenylphosphine), cobalthydridotetracarbonyl, rhodiumbis(triphenylphosphine)carbonylchloride, and rhodiumhydridobiscarbonylbis(triphenylphospine). By exchange of a ligand of the organometallic complex a phosphine or phosphite group bound to the polymer is bound to the organometallic complex.

The selectivity and the activity of the catalyst can be improved by additionally impregnating the carrier with a phosphine that can act as a ligand in the organometallic complex. Triaryl phosphines of high boiling temperature, such as triphenylphosphine and trinaphthylphosphine are preferably. The quantity of phosphine should be large enough so that under the reaction conditions the organometallic complex possesses one phosphine or phosphite ligand connected to the carrier and two other phosphine ligands.

In most cases the quantity of phosphine or phosphite groups connected to the carrier corresponds to a phosphorus content of the carrier of between about 0.05 and about 1.0% by weight. The most suitable phosphorus content seems to be a content of between about 0.1 and about 0.5% by weight. Per molecule of the transition metal complex, the catalyst may contain between about 2 and about 50 phosphine or phosphite groups bound to the carrier. After impregnation with additional phosphine, there may, in general, be between about 10 and about 200 molecules of phosphine, free as well as bound to the carrier, per molecule of the organometallic complex. A larger quantity of phosphine does not seem to present an advantage. One remarkable discovery is that the use of a relatively small quantity of additional phosphine improves both the activity and the selectivity.

The hydroformylation may be carried out at a temperature of between about 50° C. and about 140° C., and preferably between about 70° C. and about 120° C. The overall pressure may be between about 1 and about 50 bar, and is preferably between about 1 and about 25 bar. The catalyst may be used in the form of a fixed bed or a fluidized bed. Optionally, an inert particulate material may be added to the bed by way of filler material. The molar proportion between hydrogen, carbon monoxide and the olefinically unsaturated compound usually amount to about 1–10 to about 1–10 to about 1.

Unsaturated organic compounds that can be converted by means of the process according to the present invention are terminally or internally unsaturated, linear or branched aliphated monoolefins with about 2 to about 20 carbon atoms, conjugated or unconjugated diolefins with about 4 to 20 carbon atoms, cycloaliphatic and aromatic olefins with about 6 to about 20 carbon atoms, olefinically unsaturated aldehydes with 3–20 carbon atoms and the ketals derived therefrom, unsaturated alcohols, unsaturated esters, and unsaturated nitriles.

Examples of such are ethylene, propylene, butylene-1, isobutylene, butylene-2, hexene-1, octene-1, octene-4, diisobutylene, cyclohexene, styrene, butadiene, pentadiene 1-4, cyclooctadiene, acrolein, crotonaldehyde, cinnamaldehyde, 1,1-dimethoxy-propylene-2, allylalcohol, methylvinylketone, methylacrylate, methylmethacrylate, diethylmaleate, acrylonitrile. The process according to the present invention is particularly suitable for the hydroformylation of, i.e. olefins, unsaturated alcohols, unsaturated aldehydes and acetals derived therefrom.

The catalysts according to the present invention possess greater activity than catalysts which have a carrier in which phosphine or phosphite groups have been introduced by first chloromethylating the resin and subsequently converting the chloromethyl groups into phosphine groups by means of an alkalidiarylphosphine. The activity is also higher than that of catalysts having a carrier which has been phosphochlorinated with aluminiumchloride as catalyst.

The invention will be elucidated by means of the following examples without being restricted to the mode of realization described therein.

EXAMPLES

Example I

Catalysts A through D listed in Table 1 were prepared in the manner described below.

A macroporous polystyrene resin crosslinked with divinylbenzene (the commercial product XAD-2, by Serva, Federal Republic of Germany) having a particle size of between 0.1 and 1.0 mm was dried for 48 hours at a temperature of 100° C. 10 g of this resin was stirred under nitrogen with phosphorus trichloride for 30 minutes. Thereafter boron trifluorideetherate was added and the reaction mixture was heated for 2 more hours at 50° C. After that the resin particles were recovered by filtration and thoroughly washed with n-hexane and diethylether.

Subsequently the resin was reacted with an excess quantity of phenyllithium dissolved in toluene, for 3 hours at 70° C., under nitrogen. After a thorough washing treatment with, successively, toluene, methanol, water and diethylether, and drying, a resin was obtained which contained diphenylphosphine groups and in which no measurable chlorine was left. Finally the resin was stirred with a solution of rhodiumhydridocarbonyltris(triphenylphosphine) in toluene, in which, additionally, 3 mol triphenylphosphine per mol of the rhodium complex had been dissolved for stabilization. In 1 hour's time the temperature was raised to 65° C., after which the mixture was heated for 2 more hours at 65° C. under hydrogen. The resin particles were recovered from the solution by filtration under hydrogen as protective gas, and carefully washed with, successively, toluene and diethylether, to remove excess amounts of the rhodium complex and triphenylphosphine.

Catalysts B, C and D were impregnated with additional triphenylphosphine by contacting catalysts obtained in the above way with a 2.5% by weight solution of triphenylphosphine in diethylether, after which the ether was removed by evaporation.

Table 1 shows the properties of the catalysts.

Example II

Catalysts E through I listed in Table 1 were prepared in the manner described above, but with application of a resin additionally purified by extraction. This resin had been obtained by boiling 300 g of the dried resin used in Example I with, in succession, 100 ml water, methanol, diethylether and n-pentane. After each boiling treatment the resin was washed with the solvent used for this treatment and then dried. After termination of this purification the resin was dried at 90° C. for 48 more hours.

The properties of these catalysts are shown in Table 1.

TABLE 1

| Catalyst | bound P % wt. | total P % wt. | Rhodium (as metal) ppm | P/Rh (mol/mol) |
|---|---|---|---|---|
| A | 0.30 | 0.30 | 289 | 25.4 |
| B | 0.19 | 0.23 | 496 | 12.7 (15.4)* |
| C | 0.19 | 0.89 | 273 | 23.1 (108.3) |
| D | 0.07 | 0.84 | 265 | 8.8 (105.3) |

TABLE 1-continued

| Catalyst | bound P % wt. | total P % wt. | Rhodium (as metal) ppm | P/Rh (mol/mol) |
|---|---|---|---|---|
| E | 0.12 | 0.12 | 172 | 21.9 |
| F | 0.38 | 0.38 | 295 | 42.8 |
| G | 0.26 | 0.26 | 297 | 26.4 |
| H | 0.52 | 0.52 | 575 | 30.0 |
| I | 0.37 | 0.37 | 339 | 36.3 |

*The numbers given in brackets relate to the ratio of total phosphine (free and bound to resin) to the quantity of rhodium present in complex form.

The rhodium and phosphorus contents relate to the total catalyst weight.

Example III

Catalysts A through I prepared in Examples I and II were used for the hydroformylation of propylene. To this end a mixture of hydrogen, carbon monoxide and propylene in the proportion of 1:1:1 was passed across a sample of the catalyst to be examined, in a fixed-bed reactor at 90° C. and an overall pressure of 1 bar. The quantities of propylene converted and of n-butyraldehyde and iso-butyraldehyde formed were determined by gas-chromatographic analysis. No by-products were found. The catalysts examined proved to be stable for a long time under the reaction conditions applied. Table 2 shows the reaction conditions, the activity and the selectivity of the catalysts. The activity was determined after a stable level of activity had been reached. In most cases this was reached after about 40 hours.

Catalysts C, D and F were used in experiments of longer duration. The experiments with C and D were terminated after 200 hours, that the ctalyst F after 500 hours. In all cases activity and selectivity had not decreased when the experiment was terminated.

TABLE 2

| Catalyst | load mg Rh (as metal) per N cm$^3$/sec propylene throughput | activity N/cm$^3$ propylene converted per sec and per mg Rh | selectivity n/iso-butyraldehyde |
|---|---|---|---|
| A | 12.80 | 0.24 | 1.0 |
| B* | 9.26 | 1.20 | 3.8 |
| C | 13.16 | 0.69 | 16 |
| D | 13.39 | 0.26 | 18 |
| E | 7.53 | 0.18 | 0.80 |
| F | 15.03 | 0.14 | 0.85 |
| G | 14.35 | 0.37 | 0.89 |
| I | 20.40 | 0.13 | 0.75 |

*Experiment conducted at 75° C.

Example IV

Catalysts K and L listed in Table 3 were prepared by reacting phosphochlorinated divinylbenzene-styrene polymer prepared in the manner described in Example I with an excess amount of lithiummethanolate and with an excess amount of lithiumphenolate in the manner described for phenyllithium in Example I. To the resulting polymers, containing phosphite groups, the rhodium complex was bound, also in the manner described in Example I, by a treatment with rhodiumhydridocarbonyltris(triphenylphosphine), after which the catalysts were additionally impregnated with a quantity of free triphenylphosphine in the manner described in Example I.

TABLE 3

| Catalyst | bound P % wt. | total P % wt. | rhodium (as metal) ppm | P/Rh mol/mol |
|---|---|---|---|---|
| K | 0.12 | 0.19 | 1290 | 3.1 (4.9) |
| L | 0.13 | 0.19 | 893 | 4.8 (7.3) |

In catalyst K the complex was bound through the intermediacy of dimethoxyphosphite groups, in catalyst L through diphenoxyphosphite groups. In the column headed P/Rh the figures in brackets again refer to the ratio of the amount of free phosphine plus phosphorus bound as phosphite groups to the amount of rhodium.

The catalysts K and L were used in the way described in Example III for the hydroformylation of propylene. The activity of catalyst K remains at a constant level after an initial decrease, whereas the activity of catalyst L continues to decrease slowly, probably as a result of deactivation of rhodium by ortho-metallation. The hydroformylation was carried out at 70° C. and 1 bar. The molar proportion of propylene:H$_2$:CO was 1:1:1 for the experiment with catalyst K, and 1:1.5:0.4 for that carried out with catalyst L. Further data relating to catalyst L are shown in Table 4.

TABLE 4

| Catalyst | load mg Rh/N cm$^3$ propylene/sec | activity* N cm$^3$ propylene/sec/ g Rh | selectivity n/iso |
|---|---|---|---|
| K | 31.61 | 0.20 | 1.8 |
| L | 13.80 | 0.47 | 2.5 |

*measured after 100 hours.

Comparative Example

For the purpose of comparison, catalyst X was prepared so that macroreticular polystyrene resin cross-linked with divinylbenzene (the commercial product XAD-2, by Serva, FRG) was impregnated, after having been washed and dried, with a solution of rhodiumhydridocarbonyltris(triphenylphosphine) in triphenylphosphine in the way described in Netherlands Patent Application No. 7902964. The degree to which the pores were filled was 66%, the rhodium content (canculated as metal, in relation to the total catalyst weight) 0.15%, the phosphorus/rhodium ratio 81.4, and the particle size 0.42–0.50 mm.

Again for comparison, catalyst Y was prepared in which the cmplex was bound to the carrier through methylenediphenylphosphine groups. To this end the resin described in Example I was reacted with a solution of chloromethylether in hexane, in the presence of borontrifluorideetherate. The resin, containing chloromethyl groups, was thoroughly washed and dried and then reacted with an excess amount of lithiumdiphenylphosphine dissolved in tetrahydrofuran. The resulting resin, containing methylenediphenylphosphine groups was washed and dried, after which the above-mentioned rhodium complex was coupled to it in the way described in Example I. The catalyst contained 2.1% wt. bound phosphorus and 1650 ppm rhodium (calculated as metal), and the phosphorus/rhodium ratio was 42.3.

Catalysts X, Y and G were used for the hydroformylation of propylene at 90° C. and 1 bar, with a proportion of propylene:H$_2$:CO of 1:1:1. The results have been compiled in Table 5.

TABLE 5

| Catalyst | load mg Rh/N cm³ propylene/sec | activity* N cm³ propylene sec/g Rh | selectivity n/iso |
|---|---|---|---|
| X** | 29.95 | 0.075 | 24.6 |
| Y** | 88.56 | 0.19 | 3.4 |
| G | 14.35 | 0.37 | 0.89 |

*determined after 140 hours
**not according to the present invention

The activity and selectivity of catalyst X remained constant when the experiment was continued. The activity of catalyst Y continuously decreased and had become 0.16 after 240 hours, the selectivity remaining constant.

What is claimed is:

1. A process for converting an olefinically unsaturated compound to a mixture of essentially normal and iso-aldehydes with carbon monoxide and hydrogen at an elevated temperature in the presence of a catalyst comprising a macroreticular organic polymer carrier containing phosphine or phosphite groups that act as ligands for a catalytically organometallic complex, the process comprising the steps of:
   (a) preparing said catalyst by a process comprising the steps of:
      (i) phosphochlorinating said polymer with phosphorous trichloride in the presence of a borontrifluoride complex, to form chlorophosphonyl groups bound to said polymer;
      (ii) converting the chlorophosphonyl groups bound to said polymer into phosphine or phosphite groups with at least one of an alkyl hydrocarbon compound and an alkali alcoholate;
      (iii) reacting the product of step (ii) with a compound of a transition metal, a complex of a transition metal, or mixture thereof to form a catalytically active organometallic complex; and
   (b) converting said olefinically unsaturated compound in the gas phase to a mixture of essentially normal and iso-aldehydes with carbon monoxide and hydrogen at an elevated temperature in the presence of the catalyst prepared in accordance with step (a).

2. Process in accordance with claim 1, wherein said polymer carrier is a polystyrene cross-linked with divinylbenzene.

3. Process in accordance with claim 2, wherein the chlorophosphonyl groups are converted into arylphosphine groups by means of an arylalkali compound.

4. Process in accordance with claim 3, wherein the catalyst contains an amount of phosphine or phosphite groups bound to the polymer which correspond with a phosphorous content of the catalyst of between about 0.1 and about 0.5% by weight.

5. Process in accordance with claim 4, wherein the catalyst is also impregnated with a triarylphosphine with a high boiling temperature.

6. A process for making a catalyst, active for the hydroformylation of an olefinically unsaturated compound to a mixture of normal and iso-aldehydes, which process comprises the steps of:
   (a) phosphochlorinating a polymer with phosphorous trichloride in the presence of a borontrifluoride complex, to form chlorophosphonyl groups bound to said polymer;
   (b) converting said chlorophosphonyl groups bound to said polymer into phosphine or phosphite groups with at least one of an alkyl hydrocarbon compound and an alkali alcoholate; and
   (c) reacting the product of step (b) with a compound of a transition metal, a complex of a transition metal, or mixtures thereof to form a catalytically active organometallic complex.

7. A process for making a catalyst, active for the hydroformylation of an olefinically unsaturated compound to a mixture of normal and iso-aldehydes, which process comprises the steps of:
   (a) reacting a macroreticular organic polymer with phosphorus trichloride in the presence of a borontrifluoride complex to form a phosphochlorinated resin;
   (b) converting said resin with a alkali hydrocarbon or an alkali alcoholate to form a resin containing phosphine or phosphite groups; and
   (c) converting said resin containing phosphine or phosphite groups with a compound of a transition metal to form a complex, catalytically active in said hydroformylations, bound to said polymer.

8. Catalyst, obtained by the process of claims 6 or 7.

* * * * *